United States Patent [19]

Cragoe, Jr. et al.

[11] 4,181,727
[45] Jan. 1, 1980

[54] 2,3-DIHYDRO-6,7-DISUBSTITUTED-5-ACYL BENZOFURAN-2-CARBOXYLIC ACIDS

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[21] Appl. No.: 873,022

[22] Filed: Jan. 27, 1978

Related U.S. Application Data

[60] Division of Ser. No. 678,529, Apr. 20, 1976, Pat. No. 4,087,542, which is a continuation-in-part of Ser. No. 594,839, Jul. 9, 1975, abandoned.

[51] Int. Cl.$^2$ .................. A61K 31/425; C07D 275/02
[52] U.S. Cl. ....................................... 424/270; 548/134
[53] Field of Search ................... 260/302 H; 424/270

[56] References Cited

U.S. PATENT DOCUMENTS

| 3,651,094 | 3/1972 | Libis et al. | 260/346.2 |
| 3,903,114 | 9/1975 | Martret et al. | 260/332.2 |

Primary Examiner—Frederick E. Waddell
Attorney, Agent, or Firm—Michael C. Sudol, Jr.

[57] ABSTRACT

2,3-Dihydro-6,7-disubstituted-5-(acyl)benzofuran-2-carboxylic acids, the pharmaceutically acceptable salt, ester and amide derivatives thereof and combinations of these compounds with antikaluretic agents are disclosed having diuretic-saluretic, uricosuric and antihypertensive activity.

5 Claims, No Drawings

2,3-DIHYDRO-6,7-DISUBSTITUTED-5-ACYL BENZOFURAN-2-CARBOXYLIC ACIDS

This is a division of application Ser. No. 678,529, now U.S. Pat. No. 4,087,542 patented on May 2, 1978, filed Apr. 20, 1976 which is a continuatin-in-part of U.S. Ser. No. 594,839 filed July 9, 1975, now abandoned.

BACKGROUND OF THE INVENTION

This case is a continuation-in-part of our earlier filed case U.S. Ser. No. 594,839, filed in the U.S. Patent Office on July 9, 1975.

This invention relates to certain benzofurans having diuretic-saluretic, uricosuric and antihypertensive pharmacological activity. Further, this invention relates to processes for the preparation of such compounds; pharmacological compositions comprising such compounds; and to methods of treatment comprising administering such compounds and compositions to patients (both human and animal) for the alleviation of symptoms associated with electrolyte imbalance and fluid retention such as edema associated with hypertension.

The compounds of this invention may be represented by the following generic structure:

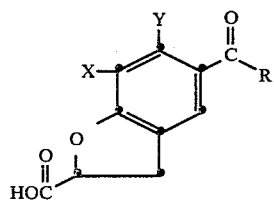

wherein
X is halo (chloro, fluoro, bromo or iodo) methyl or hydrogen;
Y is halo (chloro, fluoro, bromo or iodo) or methyl;
X and Y can be joined to form a hydrocarbylene chain containing from 3 to 4 carbon atoms, for example: 1,3-butadienylene:
R is aryl such as phenyl or mono or disubstituted phenyl wherein the substituent is halo, methyl, trifluoromethyl or methoxy; aralkyl such as benzyl or mono or dinuclear substituted aralkyl wherein the substituent is halo, methyl, methoxy or trifluoromethyl; or a heterocyclic group such as a 5 or 6 membered heterocyclic ring containing one or more atoms of oxygen, sulfur or nitrogen such as 3- or 2-thienyl, 3 or 2-furyl, 1,2,5-thiadiazolyl or substituted heterocyclics as above wherein the substituent is halo or methyl.

Also within the scope of the present invention are the pharmaceutically acceptable salt, ester and amide derivatives of the above described compounds.

For convenience, these compounds will be collectively referred to as "dihydrobenzofuran acids".

The pharmacological studies show that the instant products are effective diuretic, saluretic and uricosuric agents which can be used in the treatment of conditions associated with electrolyte and fluid retention in the treatment of hypertension. These compounds are able to maintain the uric acid concentration in the body at pretreatment levels or to even effect a decrease in the uric acid concentration when administered in therapeutic dosages in conventional vehicles.

Many of the presently available diuretics and saluretics have a tendency upon administration to induce hyperuricemia which may precipitate uric acid or sodium urate or both in the body which may cause from mild to severe cases of gout. The instant compounds of this invention now provide an effective tool to treat those patients (which includes humans and animals) requiring diuretic and saluretic treatment without incurring the risk of inducing gout. In fact, when used in appropriate doses, the compounds of this invention function as uricosuric agents.

Thus it is an object of the present invention to provide the benzofurans of the above general description and to provide processes for preparation of such compounds. Further objects of this invention are to provide pharmaceutical compositions comprising such benzofurans and to provide methods of treatment comprising administering such compounds and compositions.

DETAILED DESCRIPTION OF THE INVENTION

For purposes of description, the benzofurans of the present invention (Formula I above) may be represented according to the following structural formula:

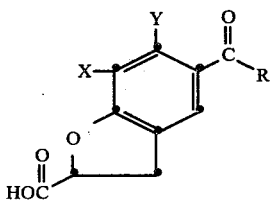

wherein X, Y and R are as previously defined.

The preferred benzofurans of the present invention are those compounds of Formula I wherein X is halo, preferably chloro, or methyl and Y is halo, preferably chloro or methyl, and the pharmaceutically acceptable salts, ester and amide derivatives thereof.

More preferred benzofurans of the present invention are those preferred compounds of Formula I wherein R is

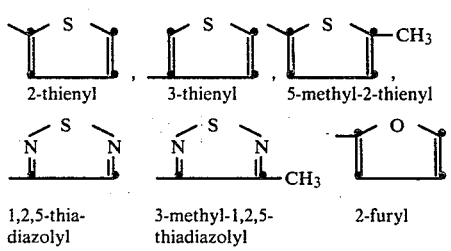

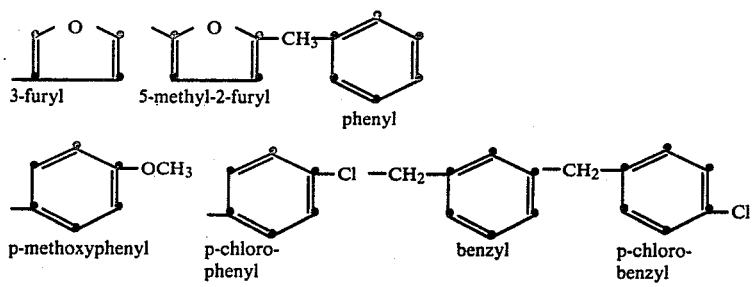

3-furyl  5-methyl-2-furyl  phenyl p-methoxyphenyl  p-chloro-phenyl  benzyl  p-chloro-benzyl and X and Y are as defined above.

Still more preferred benzofurans of the present invention are those compound of Formula II below

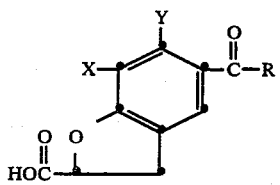

II wherein
X is chloro and
Y is chloro, and
R is an defined for the more preferred benzofurans above, and
the pharmacologically acceptable salts, ester and amide derivatives thereof.

A still more preferred aspect of the invention are those compounds of Formula II wherein X and Y are both chloro and R is

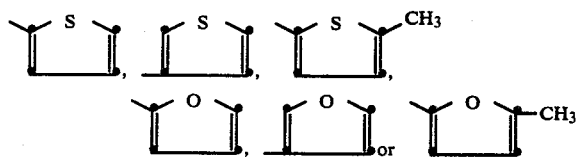

and the pharmaceutically acceptable salts, ester and amide derivatives thereof.

Several examples of specific compounds of this invention are
6,7-Dichloro-2,3-dihydro-5-(2-thenoyl)benzofuran-2-carboxylic acid;
6,7-dichloro-2,3-dihydro-5-(2-furoyl)benzofuran-2-carboxylic acid;
6,7-dichloro-2,3-dihydro-5-(5-methyl-2-thenoyl)benzofuran-2-carboxylic acid;
6,7-dichloro-2,3-dihydro-5-(3-thenoyl)benzofuran-2-carboxylic acid;
6,7-dichloro-2,3-dihydro-5-(3-furoyl)benzofuran-2-carboxylic acid;
6,7-dichloro-2,3-dihydro-5-(5-methyl-2-furoyl)benzofuran-2-carboxylic acid;
6,7-dichloro-2,3-dihydro-5-(1,2,5-Thiadiazol-3-yl)-benzofuran-2-carboxylic acid;
6,7-dichloro-2,3-dihydro-5-benzoylbenzofuran-2-carboxylic acid;
6,7-dichloro-2,3-dihydro-5-(p-methoxyphenylacetyl)-benzofuran-2-carboxylic acid.

The preferred groups of compounds depicted above have especially good diuretic, saluretic, uricosuric and antihypertensive pharmacological activity.

The benzofurans of the present invention may be prepared essentially by the reaction scheme shown below:

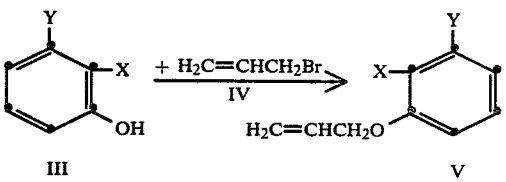

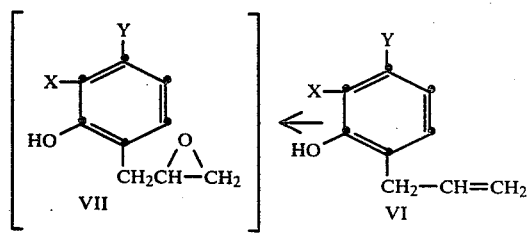

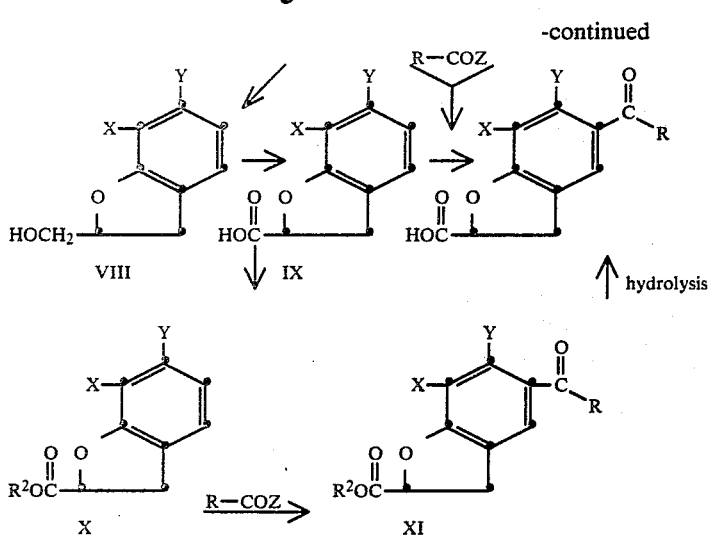

wherein X, Y and R are as defined, Z is halo and $R^2$ is lower alkyl ($C_{1-4}$).

In this reaction scheme, a 2,3-disubstituted-phenol (III) is treated with allyl bromide to yield the corresponding allyl ether (V). Typically the allyl bromide is employed in excess; in fact it may serve as the reaction solvent. Other solvents, provided they are compatible with the desired course of reaction may be employed, for example, ethanol, dimethylformamide and the like. Typically the reaction is conducted in the presence of a base such as sodium alkoxide, potassium carbonate and the like at a temperature in the range of from about 25° to about 100° C. and is substantially complete in from about 0.5 to about 2 hours. The Claisen rearrangement to obtain the 6 allyl compound (Formula VI) is effected by heating the reaction mixture at from about 100° to 220° C. The benzofuran nucleus (VIII) is obtained from the 4-allyl compound (VI) by treatment with a peracid such as m-chloroperbenzoic, peracetic acid and the like in a solvent such as methylene chloride, chloroform, acetic acid and the like at a temperature of from about 0° C. to the reflux temperature of the solvent wherein the epoxide (VII) which is initially formed cyclizes to (VIII). There are brackets around the epoxide of Formula VII to indicate that it is most generally not isolated and is an intermediate in this particular reaction step. Oxidation of the resulting hydroxymethyl-substituted-benzofuran (VII) yields the benzofurancarboxylic acid (IX).

Typically this oxidation is effected by oxidizing agents such as chromic acid, potassium permanganate and the like; the temperature of the reaction being typically in the range of from about 0° C. to the reflux temperature of the solvent which is used.

The solvent can be any inert solvent that is not effected by the reaction.

Finally the benzofurancarboxylic acid compound (Formula IX) is converted to the dihydrobenzofurancarboxylic acid compounds of the instant invention (Formula I) by reacting said compound Formula IX or its lower alkyl ($C_{1-4}$) ester X under Friedel-Crafts conditions with a carboxylic acid halide of the formula: RCOZ wherein R has been previously defined and Z is halogen such as chloro or bromo, to yield the desired product directly or by hydrolysis of the resultant ester XI. The lower alkyl ester X can be prepared from the acid IX by known esterification procedures. Suitable catalysts for the Friedel-Crafts type reaction on compounds of Formula IX are aluminum chloride, tin (IV) tetrachloride and the like. The reaction solvent and temperature are not critical inasmuch as any solvent which is inert to the acyl halide/benzofuran reactants may be employed. In this regard, suitable solvents include aliphatic and cycloaliphatic hydrocarbons such as heptane, cyclohexane, and the like; nitrohydrocarbons such as nitrobenzene and the like; and halogenated hydrocarbons such as carbon tetrachloride, methylene chloride, and the like are employable. The reaction is generally run until formation of the desired product (1) is complete, preferably from about 1 to 6 hours.

Typically the reaction is conducted from 0° C. to the reflux temperature of the particular solvent employed but temperatures up to about 100° maximum may be employed. Applicants have found that a better yield of final product (I) is obtained from compound IX by using no inert solvent but using a slight excess of the acyl halide.

As previously mentioned, the nontoxic, pharmacologically acceptable salts of the acids of Formula I and II are within the scope of this invention. These salts include those of alkali metals, alkaline earth metals and mines such as ammonia, primary and secondary amines and quaternary ammonium hydroxides. Especially preferred metal cations are those derived from alkali metals, e.g., sodium, potassium, lithium, and the like and alkaline earth metals, e.g., calcium, magnesium, and the like and other metals, e.g., aluminum, iron and zinc.

Pharmaceutically acceptable salts can be formed from ammonia, primary, secondary, or tertiary amines, or quaternary ammonium hydroxides such as methylamine, dimethylamine, trimethylamine, ethylamine, N-methylhexylamine, benzylamine, α-phenethylamine, ethylenediamine, piperidine, 1-methylpiperazine, morpholine, pyrrolidine, 1,4-dimethylpiperazine, ethanolamine, diethanolamine, triethanolamine, tris(hydroxymethyl)aminomethane, N-methylglucamine, N-methylglucosamine, ephedrine, procaine, teramethylammonium hydroxide, tetrethylammonium hydroxide, benzyltrimethylammonium and the like. These salts are particularly useful as parenteral solutions because they are very soluble in pharmaceutical carriers such as water or alcohol.

Also included within the scope of this invention are the ester and amide derivatives of the instant products which are prepared by conventional methods well known to those skilled in the art. Thus, for example, the ester derivative may be prepared by the reaction of an dihydrobenzofuran-2-carboxylic acid of this invention with an alcohol, for example, with a lower alkanol such as methanol or ethanol. The amide derivatives may be prepared by converting the same acid to its corresponding acid chloride by treatment with thionyl chloride followed by treating said acid chloride with ammonia, an appropriate mono-lower alkylamine, di-lower alkyl amine or a hetero amine, such as piperidine, morpholine and the like, to produce the corresponding amide compound. These and other equivalent methods for the preparation of the ester and amide derivatives of the instant products will be apparent to one having ordinary skill in the art and to the extent that said derivatives are both non-toxic and physiologically acceptable to the body system, said derivatives are the functional equivalent of the corresponding free acids of the present invention.

Of the non-toxic pharmaceutically acceptable salt, ester and amide derivatives of Formulae I and II, the preferred salts are those of ammonia, amines and of the alkali metals—principally sodium and potassium; the preferred esters are those derived from lower alkanols having from 1 to about 6 carbon atoms; the preferred amides are those derived from mono- and di-lower alkyl amines and hetero amines such as piperidine, morpholine and the like.

The instant compounds disclosed herein contain asymmetric carbon atom at position 2 of the benzofuran ring. The enantiomers may be separated by methods well known to those skilled in the art. This invention, therefore, embraces not only the racemic benzofurans but also the optically active enantiomers. In general, the pure enantiomers are prepared by fractional crystallization of salts of the racemic rats derived from optically active amines followed by generation of the free acid of the enantiomer by addition of an equimolar amount of a strong acid such as hydrochloric acid. Several specific isomers are (+) 6,7-dichloro-2,3-dihydro-5-(2-thenoyl)-benzofuran-2-carboxylic acid and (−) 6,7-dichloro-2,3-dihydro-5-(2-thenoyl)benzofuran-2-carboxylic acid.

Unexpectedly, the ratio of the two pharmacodynamic activities, i.e., saluretic-diuretic and uricosuric, is not necessarily the same in each enantiomer. In fact, in some instances, one property lies almost entirely in the (+)-enantiomer while the other lies in the (−)-enantiomer. For example racemic 6,7-dichloro-2,3-dihydro-5-(2-Thenonyl)benzofuran-2-carboxylic acid exhibits both potent saluretic-diuretic and uricosuric activity. The (+)-enantiomer possesses marked saluretic-diuretic activity with very little uricosuric effects while the reverse is true for the (−)enantiomer. This unique situation permits a selection of any desired ratios of the two properties by selection of the appropriate ratio of the two enantiomers. For example when various isomeric ratios of the two enantiomers of 6,7-dichloro-2,3-dihydro-5-(2-Thenoyl)-benzofuran-2-carboxylic are administered orally to chimpanzees in a total dose of 5 mg./kg., the following observations are made.

| % of Isomer | | saluresis-diuresis | Uricosuric |
|---|---|---|---|
| + | − | | |
| 100 | 0 | very marked | marginal |

-continued

| | % of Isomer | | saluresis-diuresis | Uricosuric |
|---|---|---|---|---|
| | + | − | | |
| | 75 | 25 | very marked | weak |
| (racemate) | 50 | 50 | marked | modest |
| | 25 | 75 | good | strong |
| | 12.5 | 87.5 | modest | marked |
| | 0 | 100 | marginal | very marked |

Although diuretics are often life-saving because of the above beneficial therapeutic effects, most of them have the disadvantage of causing the excretion of appreciable amounts of potassium ions. When an excessive loss of potassium ions occurs, a severe muscular weakness and feeling of extreme physical exhaustion results. The patient eliminates the unwanted sodium ions due to the action of the diuretic drugs but the undesired elimination of the potassium ions produces an imbalance that should not be allowed to persist.

This invention also involves co-administration of a dihydrobenzofurancarboxylic acid with a pyrazinolyguanidine either in the form of a salt and/or as a mixture with a hydrochloride salt of pyrazinoyl-guanidine, to thereby prevent the elimination of excessive amount of potassium ions without altering or actually increasing the amount of sodium ions that are eliminated.

To achieve the beneficial results of this invention, the preferred pyrazinolyguanidine compound is N-amidino-3,5-diamino-6-chloropyrazinecarboxamide (amiloride) or its hydrochloride salt (amiloride hydrochloride) which is described in the literature and patented arts.

Another advantage of the N-amidino-3,5-diamino-6-chloropyrazinecarboxamide salts of the dihydrobenzofurancarboxylic acid diuretics is their insolubility which makes the salts' gastrointestinal absorption slower and more gradual providing a chemical method of achieving the same effect as microencapsulation.

The examples which follow illustrate the benzofuran products of the present invention and the methods by which they are prepared. However, the examples are illustrative only and it will be apparent to those having ordinary skill in the art that all the products embraced by the above-given description of the present invention may also be prepared in an analogous manner by substituting the appropriate starting materials for those set forth in the examples.

EXAMPLE 1

(+)6,7-Dichloro-2,3-dihydro-5-(2-thenoyl)benzofuran-2-carboxylic acid

Step A: 2,3-Dichloro-6-allylphenol

A mixture of 2,3-dichlorophenol (35.5 g., 0.22 mole), allyl bromide (29.4 g., 0.24 mole) and potassium carbonate (33 g., 0.24 mole) in dimethylformamide (200 ml.) is vigorously stirred and heated at 55°–60° C. for one hour, poured into ice water, extracted with ether, washed with water and dried over magnesium sulfate. Evaporation of the ether leaves 2,3-dichlorophenyl allyl ether which is subjected to a Claisen rearrangement by heating at 250° C. for ten minutes. Distillation gives 36 g. of 2,3-dichloro-6-allylphenol which boils at 132°–4°/13 mm.

Elemental analysis for $C_9H_8Cl_2O$; Calc.: C, 53.23; H, 3.97; Found: C, 52.37; H, 3.86.

Step B:
6,7-Dichloro-2,3-dihydro-2-hydroxymethylbenzofuran

A stirred solution of sodium acetate (1 g.) in 40% peracetic acid (25 ml.) is cooled to 15° C. then treated dropwise with 2,3-dichloro-6-allylphenol. The reaction mixture is stirred at 25° C. for 48 hours, poured into excess aqueous sodium bicarbonate, extracted into ether, washed with aqueous sodium bicarbonate, water, aqueous ferrous sulfate, water, brine and dried over magnesium sulfate. Evaporation of the ether leaves 2,3-dichloro-6-(2,3-epoxypropyl)phenol which is rearranged by heating at 110° C. for ten minutes then distilled to give 10.4 g. of 6,7-dichloro-2,3-dihydro-2-hydroxymethylbenzofuran which boils at 130°/0.1 mm.

Elemental analysis for $C_9H_8Cl_2O_2$; Calc.: C, 49.34; H, 3.68; Found: C, 49.67; H, 3.74.

Step C:
6,7-Dichloro-2,3-dihydrobenzofuran-2-carboxylic acid

To a solution of 6,7-dichloro-2,3-dihydro-2-hydroxymethylbenzofuran (10.4 gm.) in acetone (200 ml.) cooled to 20° C. is added an oxidizing solution prepared from chromium trioxide (6.0 g.), concentrated sulfuric acid (5.3 ml.) and water (43 ml.) over a one-half hour period. The reaction mixture is stirred at 25° C. for 18 hours. The acetone layer is separated from the precipitated chromium salts, added to water (600 ml.) and extracted with ether (2×150 ml.). The ether extract is washed with water then extracted with aqueous sodium bicarbonate. Acidification of the basic solution gives 3.4 g. of 6,7-dichloro-2,3-dihydrobenzofuran-2-carboxylic acid which is purified by reprecipitation from aqueous sodium hydroxide with aqueous hydrochloric acid.

Elemental analysis for $C_9H_6Cl_2O_3$; Calc.: Cl, 30.43; Found: Cl, 30.29.

Step D:
(±)6,7-Dichloro-2,3-dihydro-5-(2-thenoyl)benzofuran-2-carboxylic acid To a well stirred mixture of 6,7-dichloro-2,3-dihydrobenzofuran-2-carboxylic acid (2.6 g.) and thiophene-2-carbonyl chloride (4 ml.) protected from the atmosphere with a calcium chloride tube is added anhydrous aluminum chloride (6.0 g.) over a one-hour period. The reaction mixture is heated at 80°–90° C. for 3½ hours then poured into ice water (100 ml.) and hydrochloric acid (10 ml.). The product is extracted into ether, washed with water, then extracted into aqueous sodium bicarbonate (100 ml.) from which the sodium salt of the product precipitates. The sodium salt of the product is placed in a separatory funnel with dilute hydrochloric acid (100 ml.) and ether (100 ml.) and shaken until the solid dissolves. The ether solution is washed with water, brine, dried over magnesium sulfate and the ether distilled at reduced pressure. The (±)6,7-dichloro-2,3-dihydro-5-(2-thenoyl)benzofuran-2-carboxylic acid melts at 187° C. after crystallization from butyl chloride.

Elemental analysis for $C_{14}H_8Cl_2O_4S$; Calc.: C, 49.00; H, 2.35; Found: C, 48.72, H, 2.56.

EXAMPLE 2
(±)6,7-Dichloro-2,3-dihydro-5-(2-furoyl)benzofuran-2-carboxylic acid To a well stirred mixture of 6,7-dichloro-2,3-dihydrobenzofuran-2-carboxylic acid (3.3 g.), furan-2-carbonylchloride (3.6 g.) and 200 ml methylene chloride, protected from the atmosphere with a calcium chloride tube is added anhydrous aluminum chloride (3.7 g.) over an one-half hour period. The reaction solution is stirred 18 hours at 25° C. and then refluxed for 1 hour. The solvent is removed and the residue added to ice water (200 ml.) and hydrochloric acid (20 ml.). The product is extracted into ether, washed with water, then extracted into aqueous sodium bicarbonate (200 ml.) from which the sodium salt of the product precipitates. The sodium salt of the product is placed in a separatary funnel with dilute hydrochloric acid (100 ml.) and ether (100 ml.) and shaken until the solid dissolves. The ether solution is washed with water, brine, dried over magnesium sulfate and the ether distilled at reduced pressure. The 6,7-dichloro-2,3-dihydro-5-(2-furoyl) benzofuran-2-carboxylic acid melts at 166° C. after crystallization from acetonitrile/n-butyl chloride.

Elemental analysis for $C_{14}H_8Cl_2O_5$: Calc.: C, 51.40; H, 2.46; Found: C, 51.59; H, 2.72.

EXAMPLE 3
6,7-Dichloro-2,3-dihydro-5-[3-(1,2,5-Thiadiazolyl)]benzofuran-2-carboxylic acid

Step A:
6,7-Dichloro-2,3-dihydrobenzofuran-2-carboxylic acid ethyl ester A solution of 6,7-dichloro-2,3-dihydrobenzofuran-2-carboxylic acid (70 g.) conc. sulfuric acid (2 ml.) and ethanol (250 ml.) is refluxed for 2 hours. The ethanol is distilled at reduced pressure and the residue is suspended in saturated sodium bicarbonate and extracted with ether. The ether solution is washed with brine, dried over magnesium sulfate and the ether distilled at reduced pressure. The 6,7-dichloro-2,3-dihydrobenzofuran-2-carboxylic acid ethyl ester is used without further purification in the following synthesis.

Step B:
6,7-Dichloro-2,3-dihydro-5-[3-(1,2,5-Thiadiazolyl)]benzofuran-2-carboxylic acid To a well stirred mixture of 6,7-dichloro-2,3-dihydrobenzofuran-2-carboxylic acid ethyl ester (17.5 g.) and 1,2,5-thiadiazole-3-carbonyl chloride (21.7 g.) protected from the atmosphere with a calcium chloride tube is added the anhydrous aluminum chloride (29.4 g.) over a one-half hour period. The reaction mixture is heated at 90°–95° C. for 6 hours, then poured into ice water (400 ml.) and hydrochloric acid (40 ml.). The esterified product is extracted into ether, washed with water, dried over magnesium sulfate and the ether distilled at reduced pressure. The residue was warmed (80° C.) in 2.0 N NaOH (100 ml.) for one hour to obtain the insoluble sodium salt of the product. The sodium salt of the product is placed in a separatory funnel with dilute hydrochloric acid (250 ml.) and ether (500 ml.) and shaken until the solid dissolves. The ether solution is washed with water, brine, dried over magnesium sulfate and the ether is distilled at reduced pressure. The 6,7-dichloro-2,3-dihydro-5[3-(1,2,5-Thiadiazolyl)]benzofuran-2-carboxylic acid melts at 188° C. after recrystallization from acetonitrile.

Elemental analysis for $C_{12}H_6Cl_2N_2O_4S$: Calc.: C, 41.75; H, 1.75; N, 8.12; Found: C, 41.77; H, 1.89, N, 8.06.

EXAMPLE 4

Starting with (±)6,7-dichloro-2,3-dihydro-benzofuran-2-carboxylic acid but substituting equimolar amounts of the following acyl halides in place of thiophene-2-carbonyl chloride in step D of Example 1 and following the procedure of Step D there is obtained a corresponding amount of the appropriate and product listed.

| ACID CHLORIDE | END PRODUCT |
| --- | --- |
| 5-methylthiophene-2-carbonyl chloride | (±)6,7-dichloro-2,3-dihydro-5-(5-methyl-2-thenoyl)benzofuran-2-carboxylic acid |
| thiophene-3-carbonyl chloride | (±)6,7-dichloro-2,3-dihydro-5-(3-thenoyl)benzofuran-2-carboxylic acid |
| furan-3-carbonyl chloride | (±)6,7-dichloro-2,3-dihydro-5-(3-furoyl)benzofuran-2-carboxylic acid |
| 5-methylfuran-2-carbonyl chloride | (±)6,7-dichloro-2,3-dihydro-5-(5-methyl-2-furoyl)benzofuran-2-carboxylic acid |

EXAMPLE 5

Where in Example 1, Step D, there is substituted for the (±)6,7-dichloro-2,3-dihydrobenzofuran-2-carboxylic acid an equivalent amount of (±)2,3-dihydro-6,7-dimethylbenzofuran-2-carboxylic acid, (±)2,3-dihydro-6-methylbenzofuran-2-carboxylic acid, (±)6-chloro-2,3-dihydrobenzofuran-2-carboxylic acid or (±)6-chloro-2,3-dihydro-7-methylbenzofuran-2-carboxylic acid respectively, the following compounds of this invention are obtained, respectively:

(±)2,3-dihydro-6,7-dimethyl-5-(2-thenoyl)benzofuran-2-carboxylic acid;

(±)2,3-dihydro-6-methyl-5-(2-thenoyl)benzofuran-2-carboxylic acid;

(±)6-chloro-2,3-dihydro-5-(2-thenoyl)benzofuran-2-carboxylic acid;

(±)6-chloro-2,3-dihydro-7-methyl-5-(2-thenoyl)benzofuran-2-carboxylic acid.

EXAMPLE 6

6,7-Dichloro-2,3-dihydro-5(4-methoxybenzoyl)benzofuran-2-carboxylic acid

Following the procedure of Example 2 but using an equivalent amount of anisoyl chloride in place of furan-2-carbonyl chloride used in Example 2, there is produced an equivalent amount of 6,7-Dichloro-2,3-dihydro-5-(4-methoxybenzoyl)benzofuran-2-carboxylic acid.

M.P. = 187° C.

Elemental analysis for $C_{17}H_{12}Cl_2O_5$: Calc.: C, 55.60; H, 3.29; Cl, 19.31; Found: C, 55.67; H, 3.35, Cl, 18.99.

EXAMPLE 7

6,7-Dichloro-2,3-dihydro-5-phenylacetyl benzofuran-2-carboxylic acid

Following the procedure of Example 3B but using an equivalent amount of phenyl acetyl chloride in place of 1,2,5-thiadiazole-3-carbonyl chloride and using carbon disulfide as a solvent there is produced an equivalent amount of 6,7-dichloro-2,3-dihydro-5-phenyl acetyl benzofuran-2-carboxylic acid.

M.P. = 146° C.

Elemental analysis for $C_{17}H_{12}Cl_2O_4$: Calc.: C, 58.14; H, 3.44; Found: C, 58.12; H, 3.67.

EXAMPLE 8

Resolution of the Optical Isomers of (±)6,7-dichloro-2,3-dihydro-5-(2-thenoyl)benzofuran-2-carboxylic acid Step A: (+)-isomer A mixture of racemic 6,7-dichloro-2,3-dihydro-5-(2-thenoyl)-benzofuran-2-carboxylic acid (28.0 g., 0.081 mole) and (−)-cinchonidine (24.0 g., 0.081 mole) is dissolved in hot acetonitrile (1500 ml.) and aged at 25° C. for 18 hours.

The acetonitrile is decanted from the resultant salt (28.7 g.) which is recrystallized twice from a minimum volume of acetonitrile and twice from a minimum volume of 95% ethanol affording 15.7 g. of salt of the pure (+)-enantiomer which is converted to the acid by treatment of the salt with dilute hydrochloric acid and ether. The ether phase is washed with water, dried over magnesium sulfate, and the ether distilled at reduced pressure to give the (+)-isomer.

$[\alpha]_{436}^{25} = +11.5$ (C, 1, acetone)

Step B: (−)-isomer

By following substantially the procedure described in step A, the partially resolved 6,7-dichloro-2,3-dihydro-5-(2-thenoyl)-benzofuran-2-carboxylic acid (12.0 g., 0.035 mole); (obtained from the acetonitrile mother liquor of step A) and (+)-α-methylbenzylamine (4.3 g., 0.035 mole) are mixed in acetonitrile (1000 ml.). The resultant salt (14.5 g.) was thrice recrystallized from a minimum volume of acetonitrile and ethanol (10:1) to obtain 9.4 g. of the salt of the pure (−)-enantiomer which is converted to the acid by treatment of the salt with dilute hydrochloric acid and ether.

$[\alpha]_{436}^{25} = -11.5$ (C, 1, acetone)

As mentioned previously, the novel compounds of this invention are diuretic and saluretic agents. When administered to patients in therapeutic dosages in conventional vehicles, the instant products effectively reduce the amount of sodium and chloride ions in the body, lower dangerous excesses of fluid levels to acceptable levels and in general, alleviate conditions usually associated with edema or fluid retention.

Also as mentioned previously, these compounds are able to maintain the uric acid concentration in the blood at pretreatment levels or even cause a decrease in uric acid concentration. The presence of excess uric acid in the blood can lead to crystallization of uric acid and uric acid salts in the joints causing gout. In addition hyperuricemia in conjunction with hyperlipidemia has been implicated in increasing the risk of sustaining cardiovascular heart disease.

The compounds of this invention can be administered to patients (both animal and human) as the racemic form, as either enantiomer or in a wide variety of mixtures of various ratios of the two enantiomers, each of which may be given in any of a variety of therapeutic dosages in conventional vehicles as, for example, by oral administration in the form of a tablet or by intravenous injection. In addition, the compounds may be formulated into suppositories or as a salve for topical administration or they may be administered sublinqually. Also, the daily dosage of the products may be varied over a wide range as for example, in the form of scored tablets containing 0.25, 1, 5, 10, 25, 50, 100, 150, 200, 250 and 500 milligrams of the active ingredient for the symptomatic adjustment of the dosage to the patient to be treated. These dosages are well below the toxic or lethal dose of the products.

A suitable unit dosage form of the product of this invention can be administered by mixing 25 mg. of a dihydrobenzofuran or a suitable salt, ester or amide derivative thereof of the present invention with 174 mg. of lactose and 1 mg. of magnesium stearate and placing the 200 mg. mixture into a No. 1 gelatin capsule. Similarly by employing more of the active ingredient and less lactose, other dosage forms can be put up in No. 1 gelatin capsules and should it be necessary to mix more than 200 mg. of ingredients together larger capsules may be employed. Compressed tablets, pills or other desired unit dosages can be prepared to incorporate the compounds of this invention by conventional methods and if desired can be made up as elixirs or as injectable solutions by methods well known to pharmacists.

An effective amount of the product is ordinarily supplied at a unit dosage level of from about 0.003 mg. to about 10 mg./kg. of body weight of the patient. Preferably the range is from about 0.01 mg. to about 1.5 mg./kg. with a most preferred dose being about 0.07 to 0.35 mg./kg. of body weight. The unit dose can be administered as infrequently as twice per week to as frequently as 3 times per day.

It is also within the scope of this invention to combine two or more of the compounds of this invention into a unit dosage form or to combine one or more of the compounds of this invention with other known diuretics and saluretics or with other desired therapeutic and/or nutritive agents in dosage unit form.

The present invention embraces such compositions administration to patients, preferably by oral administration, wherein the potassium conserving diuretic, N-amidino-3,5-diamino-6-chloropyrazinecarboxamide hydrochloride, hereinafter referred to as amiloride hydrochloride, is present as a physical mixture in combination with the dihydrobenzofurans of the present invention. The present invention embraces compositions wherein the molar ratio of the dihydrobenzofuran to amiloride hydrochloride ranges from about 50:1 to 1:1. The preferred ratios of the dihydrobenzofuran to amiloride hydrochloride ranges from 25:1 to 1:1.

EXAMPLE 9

|  | Per Capsule |
|---|---|
| (±)6,7-Dichloro-2,3-dihydro-5-(2-thenoyl)-benzofuran-2-carboxylic | 25 mg. |
| Lactose | 174 mg. |
| Magnesium Stearate | 1 mg. |
| Capsule (Size No. 1) | 200 mg. |

The (±)6,7-dichloro-2,3-dihydro-5-(2-thenoyl)-benzofuran-2-carboxylic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

Similar dry-filled capsules are prepared by replacing the active ingredient of the above example by the sodium, diethanolamine, and triethanolamine salt thereof, respectively.

Similarly dry filled capsules can be prepared by replacing the active ingredient of the above example by a molar equivalent amount of any of the other novel compounds of this invention.

EXAMPLES 10-16

Following the procedure for combining the ingredients as described in Example 9, the following dry filled capsules can be prepared.

Similar dry filled capsules can be prepared by replacing the benzofuran active ingredient of the above examples by the sodium, diethanol amine and triethanolamine and salts thereof, respectively. Also dry filled capsules can be prepared by replacing the benzofuran active ingredient of the above examples by a molar equivalent of any of the other compounds of this invention.

EXAMPLE 10

|  | Per Capsule |
|---|---|
| (+)-5,7-Dichloro-2,3-dihydro-5-(2-thenoyl)benzofuran-2-carboxylic acid | 15 mg. |
| Lactose | 184 mg. |
| Magnesium stearate | 1 mg. |
| Capsule (Size No. 1) | 200 mg. |

EXAMPLE 11

|  | Per Capsule |
|---|---|
| (+)6,7-Dichloro-2,3-dihydro-5-(2-thenoyl)benzofuran-2-carboxylic acid | 15 mg. |
| (−)6,7-Dichloro-2,3:dihydro-5(2-thenoyl)benzofuran-2-carboxylic acid | 30 mg. |
| Lactose | 154 mg. |
| Magnesium stearate | 1 mg. |
| Capsule (Size No. 1) | 200 mg. |

EXAMPLE 12

|  | Per Capsule |
|---|---|
| (+)-6,7-Dichloro-2,3-dihydro-5-(2-thenoyl)benzofuran-2-carboxylic acid | 10 mg. |
| (−)6,7-Dichloro-2,3-dihydro-5-(2-thenoyl)benzofuran-2-carboxylic acid | 30 mg. |
| Lactose | 159 mg. |
| Magnesium stearate | 1 mg. |
| Capsule (Size No. 1) | 200 mg. |

EXAMPLE 13

|  | Per Capsule |
|---|---|
| (±)6,7-Dichloro-2,3-dihydro-5-(2 thenoyl)benzofuran-2-carboxylic acid | 20 mg. |
| (−)6,7-Dichloro-2,3-dihydro-5-(2-thenoyl)benzopfuran-2-carboxylic acid | 30 mg. |
| Lactose | 149 mg. |
| Magnesium stearate | 1 mg. |
| Capsule (Size No. 1) | 200 mg. |

EXAMPLE 13

|  | Per Capsule |
|---|---|
| (±)6,7-Dichloro-2,3-dihydro-5-(2-thenoyl)benzofuran-2-carboxylic acid | 20 mg. |
| (−)6,7-Dichloro-2,3-dihydro-5-(2-thenoyl)benzofuran-2-carboxylic acid | 30 mg. |

-continued

|  | Per Capsule |
|---|---|
| Lactose | 149 mg. |
| Magnesium stearate | 1 mg. |
| Capsule (Size No. 1) | 200 mg. |

EXAMPLE 14

|  | Per Capsule |
|---|---|
| 6,7-Dichloro-2,3-dihydro-5-(2-furoyl)benzofuran-2-carboxylic acid | 25 mg. |
| Lactose | 179 mg. |
| Magnesium stearate | 1 mg. |
| Capsule (Size No. 1) | 200 mg. |

EXAMPLE 15

|  | Per Capsule |
|---|---|
| (±)6,7-Dichloro-2,3-dihydro-5-(2-thenoyl)benzofuran-2-carboxylic acid | 20 mg. |
| N-amidino-3,5-diamino-6-chloropyrazine-carboxamide hydrochloride dihydrate | 5 mg. |
| Lactose | 174 mg. |
| Magnesium stearate | 1 mg. |
| Capsule (Size No. 1) | 200 mg. |

EXAMPLE 16

|  | Per Capsule |
|---|---|
| (±)6,7-Dichloro-2,3-dihydro-5-(2-thenoyl)benzofuran-2-carboxylic acid | 20 mg. |
| (+)6,7-Dichloro-2,3-dihydro-5-(2-thenoyl)benzofuran-2-carboxylic acid | 20 mg. |
| N-amidino-3,5-diamino-6-chloropyrazine-carboxamide hydrochloride dihydrate | 5 mg. |
| Lactose | 154 mg. |
| Magnesium stearate | 1 mg. |
| Capsule (Size No. 1) | 200 mg. |

What is claimed is:

1. A compound of the formula

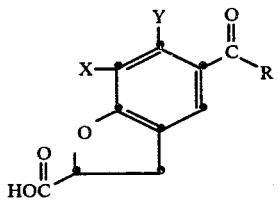

wherein

X is halo, methyl or hydrogen;
Y is halo or methyl;
X and Y can be combined to form a hydrocarbylene radical of from 3 to 4 carbon atoms;
R is selected from the group consisting of 1,2,5-thiadiazyl or 3-methyl-1,2,5-thiadiazyl and
the non-toxic pharmaceutically acceptable salt, ester and amide derivative thereof.

2. The compound of claim 1 wherein X and Y are both chloro.

3. The (+) and (−) isomers of the compound of claim 2.

4. A pharmaceutical composition useful in the treatment of edema associated with hypertension comprising a therapeutically effective amount of a compound of the formula:

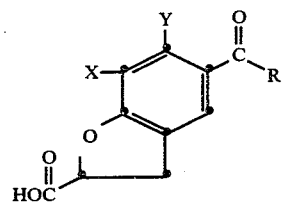

wherein
X is chloro;
Y is chloro; and
R is selected from the group consisting of 1,2,5-thiadiazyl or 3-methyl-1,2,5-thiadiazyl and
the non-toxic pharmaceutically acceptable salt, ester and amide derivative thereof and a pharmaceutically acceptable carrier.

5. A method of treatment of edema associated with hypertension comprising the administration to a patient of from 0.01 mg. to 10 mg./kg of body weight of the patient of a compound having the formula:

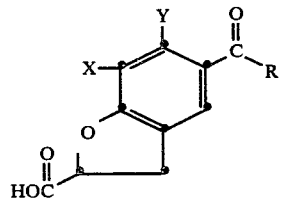

wherein
X is chloro;
Y is chloro; and
R is selected from the group consisting of 1,2,5-thiadiazyl or 3-methyl-1,2,5-thiadiazyl and
the non-toxic pharmaceutically acceptable salt, ester and amide derivative thereof.

* * * * *